(12) United States Patent
Sakuragi

(10) Patent No.: US 12,089,976 B2
(45) Date of Patent: *Sep. 17, 2024

(54) REGION CORRECTION APPARATUS, REGION CORRECTION METHOD, AND REGION CORRECTION PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 605 days.

This patent is subject to a terminal disclaimer.

(21) Appl. No.: 17/233,524

(22) Filed: Apr. 18, 2021

(65) Prior Publication Data
US 2021/0256741 A1 Aug. 19, 2021

Related U.S. Application Data

(63) Continuation of application No. PCT/JP2019/040490, filed on Oct. 15, 2019.

(30) Foreign Application Priority Data

Oct. 31, 2018 (JP) ................................. 2018-205733

(51) Int. Cl.
*A61B 6/46* (2024.01)
*A61B 6/03* (2006.01)
(Continued)

(52) U.S. Cl.
CPC .............. *A61B 6/469* (2013.01); *A61B 6/032* (2013.01); *A61B 6/463* (2013.01); *G06T 11/008* (2013.01);
(Continued)

(58) Field of Classification Search
CPC ............. G06T 2219/008; G06T 11/008; G06T 2210/41; G06T 2207/30004; G06V 10/22; G06V 10/25
See application file for complete search history.

(56) References Cited

U.S. PATENT DOCUMENTS 11,715,279 B2 * 8/2023 Hashimoto ............... G06T 7/00
382/128
2008/0267481 A1* 10/2008 Nakamura ........... G06V 10/987
382/131
(Continued)

FOREIGN PATENT DOCUMENTS

JP H1057371 3/1998
JP 2002210027 7/2002
(Continued)

OTHER PUBLICATIONS

"International Search Report (Form PCT/ISA/210) of PCT/JP2019/040490," mailed on Dec. 10, 2019, with English translation thereof, pp. 1-5.

(Continued)

*Primary Examiner* — Ross Varndell
(74) *Attorney, Agent, or Firm* — JCIPRNET

(57) ABSTRACT

The display controller displays a first tomographic image of a three-dimensional image consisting of a plurality of tomographic images on a display unit. A first correction unit corrects the boundary of a first region of interest extracted from the first tomographic image, by a correction instruction using a correction instruction region for the boundary of the first region of interest. The first instruction region setting unit sets a first instruction region on a second tomographic image of the plurality of tomographic images. The second correction unit corrects the boundary of a second region of interest extracted from the second tomographic image by setting a second instruction region on the second tomographic image.

8 Claims, 10 Drawing Sheets

(51) Int. Cl.
*G06T 11/00* (2006.01)
*G06V 10/25* (2022.01)
*G06V 10/44* (2022.01)
*G06V 10/98* (2022.01)

(52) U.S. Cl.
CPC .............. *G06V 10/25* (2022.01); *G06V 10/44* (2022.01); *G06V 10/98* (2022.01); *G06V 2201/03* (2022.01)

(56) References Cited

U.S. PATENT DOCUMENTS

| | | | |
|---|---|---|---|
| 2009/0257550 A1* | 10/2009 | Moriya | G06T 19/00 378/4 |
| 2012/0002850 A1 | 1/2012 | Ijiri et al. | |
| 2014/0286551 A1* | 9/2014 | Yoshida | G06T 7/0012 382/128 |
| 2022/0076462 A1* | 3/2022 | Yuzawa | A61B 6/463 |

FOREIGN PATENT DOCUMENTS

| | | |
|---|---|---|
| JP | 2005224460 | 8/2005 |
| JP | 2012014360 | 1/2012 |
| JP | 2018036852 | 3/2018 |

OTHER PUBLICATIONS

"Written Opinion of the International Searching Authority (Form PCT/ISA/237) of PCT/JP2019/040490," mailed on Dec. 10, 2019, with English translation thereof, pp. 1-8.

* cited by examiner

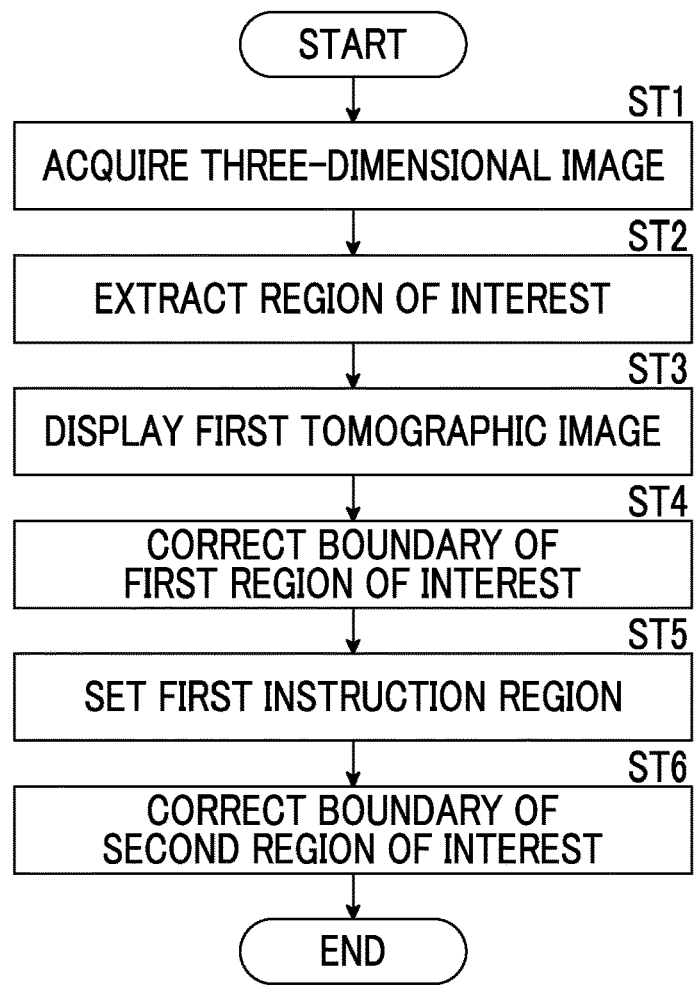
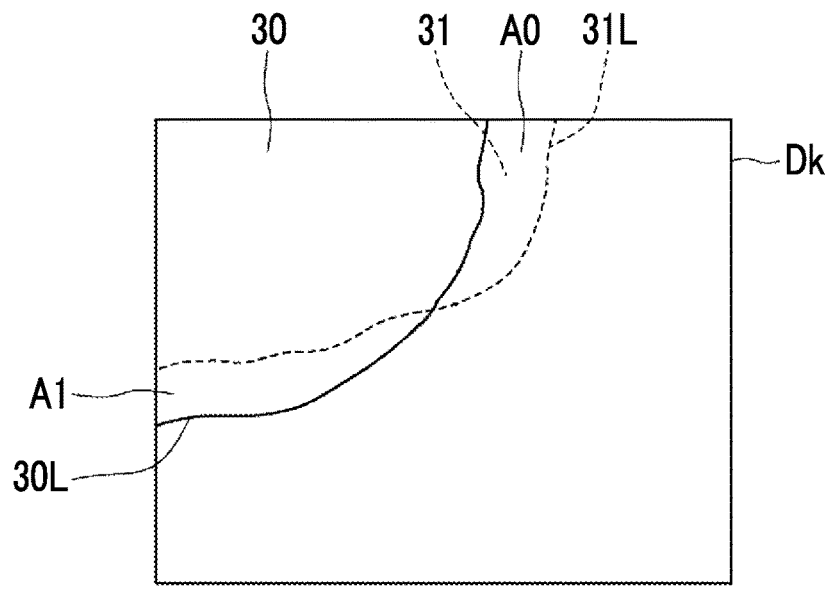

REGION CORRECTION APPARATUS, REGION CORRECTION METHOD, AND REGION CORRECTION PROGRAM

CROSS REFERENCE TO RELATED APPLICATIONS

The present application is a Continuation of PCT International Application No. PCT/JP2019/040490 filed on Oct. 15, 2019, which claims priority under 35 U.S.C. § 119(a) to Japanese Patent Application No. 2018-205733 filed on Oct. 31, 2018. Each of the above applications is hereby expressly incorporated by reference, in its entirety, into the present application.

BACKGROUND

Technical Field

The present disclosure relates to a region correction apparatus, a region correction method, and a region correction program that correct the boundary of a region of interest extracted from a three-dimensional image.

Related Art

In recent years, advances in medical equipment such as a computed tomography (CT) apparatus and a magnetic resonance imaging (MRI) apparatus have made it possible to perform diagnostic imaging using a higher quality three-dimensional image having higher resolution. A region of interest such as an organ and a lesion included in such a three-dimensional image has also been automatically extracted. However, in a case of automatically extracting the region of interest, over-extraction and under-extraction may occur. In such a case, it is necessary to correct the boundaries of the region of interest which is automatically extracted.

As a method of correcting the boundaries, the deletion of the over-extracted portion or the addition of the under-extracted portion with respect to the region of interest has been performed by displaying two-dimensional tomographic images constituting a three-dimensional image and moving a cursor having a predetermined shape such as a circle in the displayed tomographic images. However, in a case of correcting the boundaries of the regions of interest included in the tomographic images, the boundaries in a direction in which the tomographic images are arranged may not be smoothly connected to each other. When the three-dimensional image is viewed in a direction intersecting the direction in which the tomographic images are arranged, the boundaries of the regions of interest may not be smoothly connected to each other.

Thus, it is conceivable to three-dimensionally correct the boundaries of the regions of interest in the three-dimensional image by using a spherical cursor. However, the boundaries in the direction in which the tomographic images are arranged have not a spherical shape. Therefore, in a case of using the spherical cursor, an unintended overcorrection may occur.

In addition, a method that sets regions of interest in the two tomographic images among the plurality of tomographic images constituting the three-dimensional image and interpolates the regions of interest set in the two tomographic images to the tomographic images present between the two tomographic images, to set a region of interest, has been proposed (JP1998-057371A (JP-H10-057371A)). Further, a method that performs deformation operation of the contour line in the designated tomographic plane in the tomographic images constituting the three-dimensional image to perform deformation operation of the contour line in another tomographic plane, has also been proposed (JP2012-014360A).

Incidentally, the method described in JP1998-057371A (JP-H10-057371A) needs to set regions of interest in the two tomographic images, which imposes a heavy burden on the operator. Further, the method described in JP2012-014360A needs to obtain contour information for the plurality of tomographic images, which requires a long time for the processing.

SUMMARY OF THE INVENTION

The present invention has been made in view of the above circumstances, and an object thereof is to make it possible to correct the boundary of a region of interest by simple computation while reducing the burden on an operator.

A region correction apparatus according to the present disclosure comprises:
- a display controller that displays a first tomographic image of a three-dimensional image consisting of a plurality of tomographic images;
- a first correction unit that corrects a boundary of a first region of interest extracted from the displayed first tomographic image, by a correction instruction using a correction instruction region for the boundary of the first region of interest;
- a first instruction region setting unit that sets a first instruction region on at least one second tomographic image of the plurality of tomographic images based on a first correction region added or deleted by the correction in the first tomographic image and the correction instruction region; and
- a second correction unit that corrects a boundary of a second region of interest extracted from the second tomographic image by setting a second instruction region on the second tomographic image based on the first instruction region and the correction instruction region.

In addition, in the region correction apparatus according to the present disclosure, the first instruction region setting unit may set the first instruction region that has a size smaller than that of the correction instruction region as a distance between the first tomographic image and the second tomographic image increases.

Further, in the region correction apparatus according to the present disclosure, the second correction unit may set the second instruction region by expanding the first instruction region based on information regarding an inside of a region of the second tomographic image corresponding to the correction instruction region.

Furthermore, in the region correction apparatus according to the present disclosure, the second correction unit may set the second instruction region having a shape corresponding to a boundary of a region of interest included in the second tomographic image.

Further, in the region correction apparatus according to the present disclosure, the second tomographic image may be included within a predetermined distance from the first tomographic image.

In addition, the region correction apparatus according to the present disclosure may further comprise a region-of-interest extraction unit that extracts a region of interest from each of the plurality of tomographic images.

A region correction method according to the present disclosure comprises:

displaying a first tomographic image of a three-dimensional image consisting of a plurality of tomographic images;

correcting a boundary of a first region of interest extracted from the displayed first tomographic image, by a correction instruction using a correction instruction region for the boundary of the first region of interest;

setting a first instruction region on at least one second tomographic image of the plurality of tomographic images based on a first correction region added or deleted by the correction in the first tomographic image and the correction instruction region; and correcting a boundary of a second region of interest extracted from the second tomographic image by setting a second instruction region on the second tomographic image based on the first instruction region and the correction instruction region.

Moreover, the region correction method according to the present disclosure may also be provided as a program to be executed by a computer.

Another region correction apparatus according to the present disclosure comprises:

a memory that stores a command to be executed by a computer; and a processor configured to execute the stored command, in which the processor executes a process of displaying a first tomographic image of a three-dimensional image consisting of a plurality of tomographic images;

correcting a boundary of a first region of interest extracted from the displayed first tomographic image, by a correction instruction using a correction instruction region for the boundary of the first region of interest;

setting a first instruction region on at least one second tomographic image of the plurality of tomographic images based on a first correction region added or deleted by the correction in the first tomographic image and the correction instruction region; and correcting a boundary of a second region of interest extracted from the second tomographic image by setting a second instruction region on the second tomographic image based on the first instruction region and the correction instruction region.

According to the present disclosure, it is possible to correct the boundary of the region of interest by simple computation while reducing the burden on the operator.

BRIEF DESCRIPTION OF THE DRAWINGS

FIG. 3 is a flowchart showing processing performed in the present embodiment.

FIG. 4 is a diagram showing a first tomographic image displayed on a display unit.

DETAILED DESCRIPTION

Figure 1:
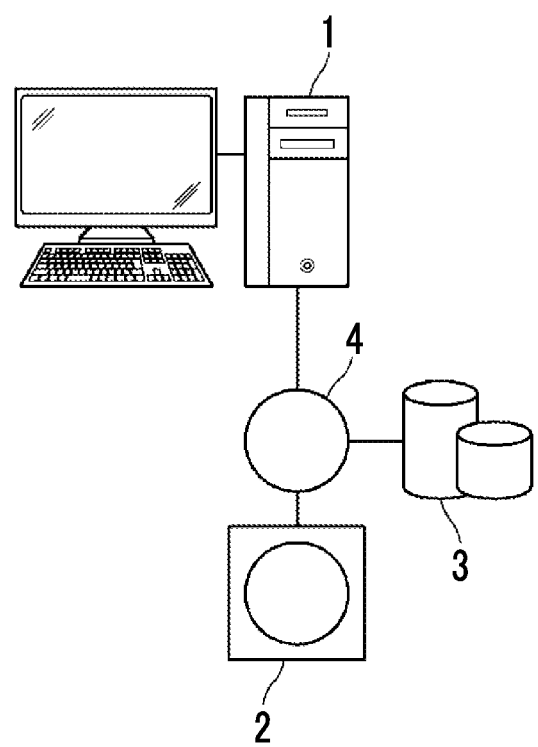
FIG. 1 is a hardware configuration diagram showing an outline of a diagnosis support system to which a region correction apparatus according to an embodiment of the present disclosure is applied.

Hereinafter, an embodiment of the present disclosure will be described with reference to the drawings. FIG. 1 is a hardware configuration diagram showing an outline of a diagnosis support system to which a region correction apparatus according to the embodiment of the present disclosure is applied. As shown in FIG. 1, in the diagnosis support system, a region correction apparatus 1, a three-dimensional image capturing apparatus 2, and an image storage server 3 according to the present embodiment are connected to communicate with one another via a network 4.

The three-dimensional image capturing apparatus 2 is an apparatus that generates a three-dimensional image representing a site of a subject as a diagnosis target by capturing the site, and specific examples thereof include a CT apparatus, an MRI apparatus, and a positron emission tomography (PET) apparatus. The three-dimensional image generated by the three-dimensional image capturing apparatus 2 is transmitted to and stored in the image storage server 3. In the present embodiment, the three-dimensional image capturing apparatus 2 is a CT apparatus, and a CT image including a site of a subject as a diagnosis target is generated as a three-dimensional image G0. In addition, the three-dimensional image G0 consists of a plurality of tomographic images.

The image storage server 3 is a computer that stores and manages various data, and comprises a large-capacity external storage device and database management software. The image storage server 3 communicates with another apparatus via a wired or wireless network 4 to transmit and receive image data and the like. Specifically, the image storage server 3 acquires various data including the image data of the three-dimensional image G0 generated by the three-dimensional image capturing apparatus 2 via the network, and stores and manages the acquired data in a recording medium such as a large-capacity external storage device. A storage format of the image data and a communication between the apparatuses via the network 4 are based on a protocol such as digital imaging and communication in medicine (DICOM).

The region correction apparatus 1 is an apparatus, as one computer on which the region correction program according to the present embodiment is installed. The computer may be a workstation or a personal computer directly operated by a doctor who performs diagnosis, or may be a server computer connected to the workstation or the personal computer via a network. The region correction program is distributed by being recorded in a recording medium such as a digital versatile disc (DVD) or a compact disc read only memory (CD-ROM), and is installed on a computer from the recording medium. Alternatively, the region correction program is stored in a storage device of a server computer or a network storage connected to the network to be accessible from the outside, and is downloaded and installed on the computer which is used by the doctor according to a request.

Figure 2:
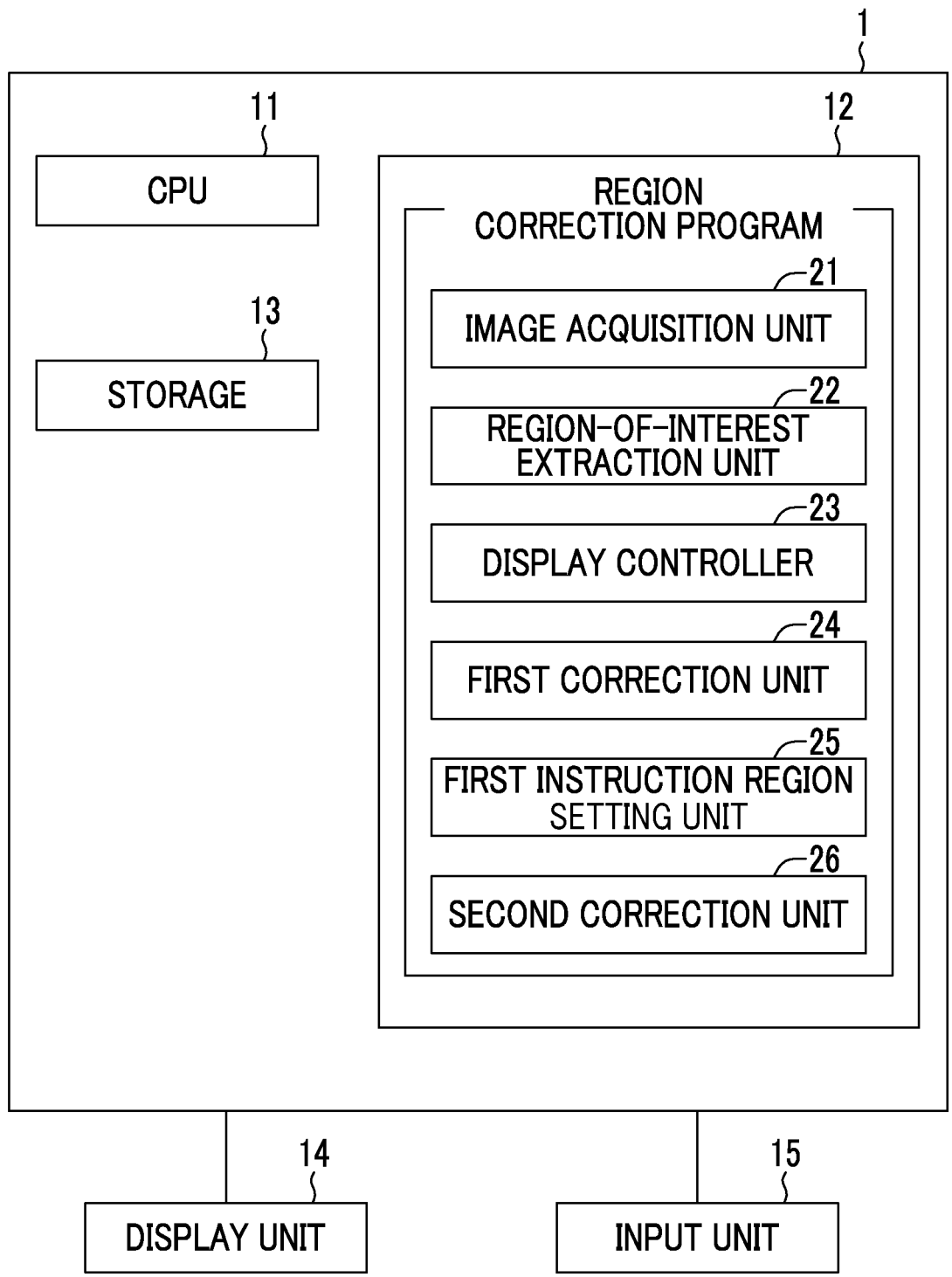
FIG. 2 is a diagram showing a schematic configuration of the region correction apparatus according to the embodiment of the present disclosure.

FIG. 2 is a diagram showing the schematic configuration of the region correction apparatus which is realized by installing the region correction program on a computer. As shown in FIG. 2, the region correction apparatus 1 comprises a central processing unit (CPU) 11, a memory 12, and a storage 13 as a standard workstation configuration. Further, a display unit 14 such as a liquid crystal display, and an input unit 15 such as a keyboard and a mouse are connected to the region correction apparatus 1.

The storage 13 is provided with a hard disk drive or the like, and stores the three-dimensional image G0 acquired from the image storage server 3 via the network 4 and various information including information necessary for processing.

Further, the region correction program is stored in the memory 12. As processing to be executed by the CPU 11, the region correction program defines image acquisition processing that acquires the three-dimensional image G0; region-of-interest extraction processing that extracts a region of interest from each of the plurality of tomographic images constituting the three-dimensional image G0; display control processing that displays a first tomographic image among the plurality of tomographic images on a display unit 14; first correction processing that corrects the boundary of a first region of interest included in the displayed first tomographic image, by a correction instruction using a correction instruction region for the boundary of the first region of interest; first instruction region setting processing that sets a first instruction region on at least one second tomographic image adjacent to the first tomographic image based on the first correction region added or deleted by the correction in the first tomographic image and the correction instruction region; and second correction processing that corrects the boundary of a second region of interest extracted from the second tomographic image by setting a second instruction region on the second tomographic image based on the first instruction region and the correction instruction region.

The CPU 11 executes the processing according to the program, and thereby the computer functions as an image acquisition unit 21, a region-of-interest extraction unit 22, a display controller 23, a first correction unit 24, a first instruction region setting unit 25, and a second correction unit 26.

The image acquisition unit 21 acquires the three-dimensional image G0 including the region of interest from the image storage server 3. The region of interest is, for example, a region of an organization such as an organ, a bone, and a cartilage that the user is interested in, as a diagnosis target. In a case where the three-dimensional image G0 is already stored in the storage 13, the image acquisition unit 21 may acquire the three-dimensional image G0 from the storage 13.

The region-of-interest extraction unit 22 extracts a region of interest from the three-dimensional image G0. For the extraction of the region of interest, the region-of-interest extraction unit 22 comprises a learned model obtained by performing machine learning so as to extract the region of interest from the three-dimensional image G0. The learned model is provided with a neural network obtained by performing deep learning so as to extract, as a region of interest, an organization such as an organ, a bone, and a cartilage as a diagnosis target. Examples of the organ as a diagnosis target include the heart, liver, lungs, kidneys, and brain. In a case where the three-dimensional image G0 is received, the learned model outputs a determination result representing whether or not each pixel of the three-dimensional image G0 corresponds to a region of interest. The region-of-interest extraction unit 22 extracts a region consisting of pixels determined to correspond to a region of interest, as a region of interest.

In addition to the neural network obtained by performing deep learning, the learned model may be provided with, for example, a support vector machine (SVM), a convolutional neural network (CNN), and a recurrent neural network (RNN). However, the region-of-interest extraction unit 22 is not limited to a unit provided with the learned model obtained by performing machine learning. For example, the region of interest may be extracted by template matching or the like.

Hereinafter, processing performed by the display controller 23, the first correction unit 24, the first instruction region setting unit 25, and the second correction unit 26 will be described. FIG. 3 is a flowchart showing processing performed in the present embodiment. First, the image acquisition unit 21 acquires a three-dimensional image G0 (Step ST1). Next, the region-of-interest extraction unit 22 extracts a region of interest from the three-dimensional image G0 (Step ST2). The display controller 23 displays a first tomographic image Dk among the plurality of tomographic images Dj (j=1 to n, n is the number of tomographic images) constituting the three-dimensional image G0, on the display unit 14 (Step ST3). The first tomographic image Dk to be displayed may be a tomographic image having any cross section of an axial cross section, a sagittal cross section, or a coronal cross section.

FIG. 4 is a diagram showing the first tomographic image Dk displayed on the display unit 14. As shown in FIG. 4, the first tomographic image Dk includes the boundary 30L of the extracted first region of interest 30. The first region of interest 30 is included in the first tomographic image Dk, as a mask. The mask may be represented only by a contour thereof, or may be subjected to hatching or filled with a predetermined color. In the following description, it is assumed that the first region of interest 30 means a masked region in the first tomographic image Dk. Here, the extraction result by the region-of-interest extraction unit 22 is not always accurate, and the first region of interest 30 may not match with the actual region of interest 31 included in the first tomographic image Dk. FIG. 4 shows the boundary 31L of the actual region of interest 31 by a broken line. In such a case, as shown in FIG. 4, it is necessary to add the under-extracted region A0 to the first region of interest 30 and delete the over-extracted region A1 from the first region of interest 30. Thus, the user corrects the boundary 30L of the extracted first region of interest 30 by using the input unit 15.

In a case where the user inputs a correction instruction through the input unit 15, the first correction unit 24 displays a circular cursor 40 on the display unit 14 and receives the correction instruction using the cursor 40 by the user. In this case, the user moves the cursor 40 by using the mouse of the input unit 15 to give the correction instruction so that the boundary 30L of the first region of interest 30 coincides with the boundary 31L of the actual region of interest 31. The first correction unit 24 corrects the boundary 30L of the first region of interest 30 in accordance with the correction instruction by the user (Step ST4). The shape of the cursor 40 is not limited to a circle, and may be any shape such as a rectangular shape, a triangular shape, and an arrow shape. Further, the cursor 40 corresponds to a correction instruction region of the present disclosure.

Figure 5:
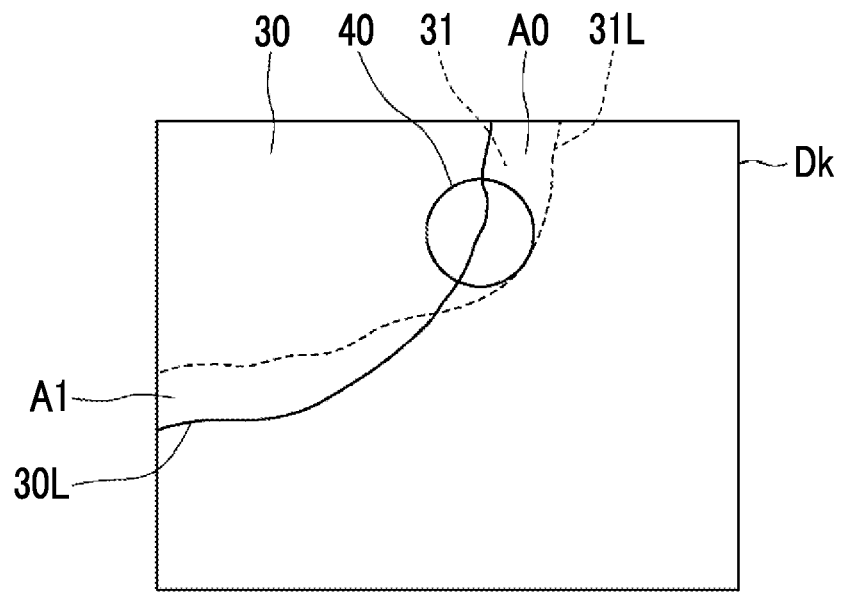
FIG. 5 is a diagram for explaining a correction instruction using a cursor.
Figure 6:
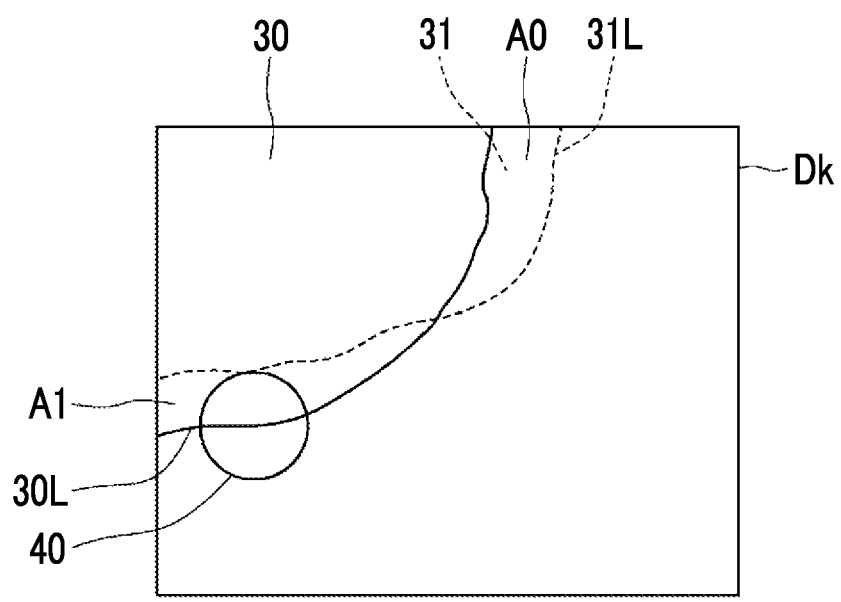
FIG. 6 is a diagram for explaining another correction instruction using the cursor.
Figure 7:
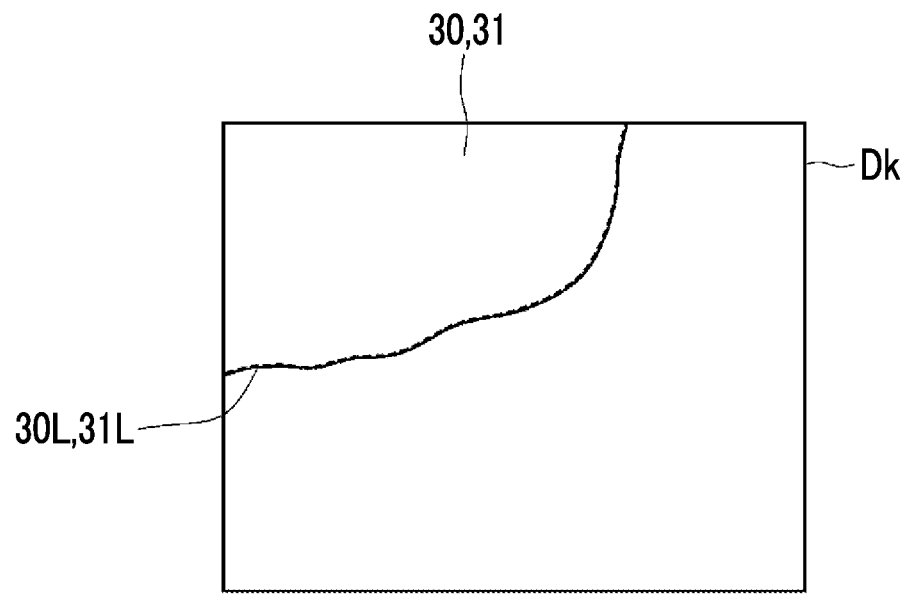
FIG. 7 is a diagram for explaining correction of a boundary of a first region of interest.

FIGS. 5 and 6 are diagrams for explaining the correction instruction using the cursor. As shown in FIG. 5, while the user gives a region addition instruction, for the region A0 by which the first region of interest 30 with respect to the actual region of interest 31 is under-extracted, the user moves an outer edge of the cursor 40 along the boundary 31L of the actual region of interest 31, thereby giving the instruction on adding the under-extracted region A0 to the first region of interest 30. The region addition instruction may be given, for example, by a left click of the mouse as the input unit 15 or a predetermined combination of pressing of a cursor and a click of the mouse, but the method thereof is not limited thereto. On the other hand, as shown in FIG. 6, while the user gives a region deletion instruction, for the region A1 by which the first region of interest 30 with respect to the actual region of interest 31 is over-extracted, the user moves the outer edge of the cursor 40 along the boundary 31L of the actual region of interest 31, thereby giving the instruction on deleting the over-extracted region A1 from the first region of interest 30. The region deletion instruction may be given, for example, by a left click of the mouse as the input unit 15 or a predetermined combination of pressing of a cursor and a click of the mouse, but the method thereof is not limited thereto. As a result, as shown in FIG. 7, the boundary 30L of the first region of interest 30 coincides with the boundary 31L of the actual region of interest 31.

Meanwhile, the first instruction region setting unit 25 sets a first instruction region on a second tomographic image Dk+1 adjacent to the first tomographic image Dk, based on the cursor 40 or the first correction region added or deleted by the correction for the boundary 30L of the first region of interest 30 by the first correction unit 24 (Step ST5). First, the processing in a case where the first correction region is an added region will be described.

Figure 8:
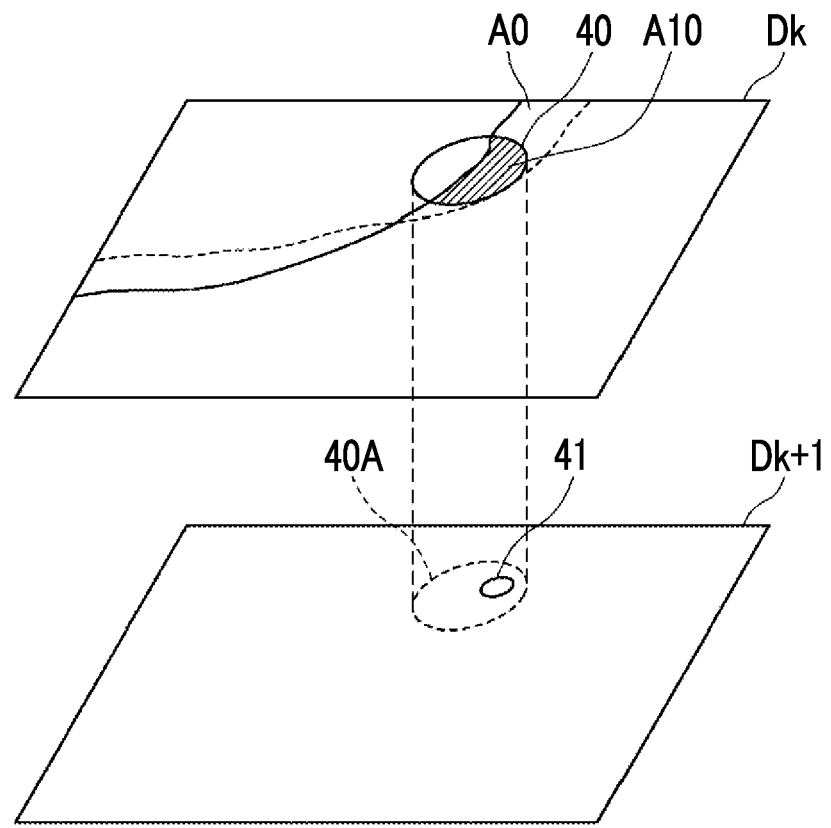
FIG. 8 is a diagram for explaining setting of a first instruction region in a case where a first correction region is an added region.

FIG. 8 is a diagram for explaining the setting of the first instruction region in a case where the first correction region is an added region. As shown in FIG. 8, in a case where the first correction region A10 indicated by the diagonal lines is added, by using the cursor 40, to the region A0 by which the first region of interest 30 is under-extracted, the first instruction region setting unit 25 sets a circular first instruction region 41 having a size smaller than that of the cursor 40 at a position on the second tomographic image Dk+1 which corresponds to the first correction region A10 added into the cursor 40. The broken line in the second tomographic image Dk+1 represents the contour of the cursor-corresponding region 40A corresponding to the cursor 40 in the first tomographic image Dk. The size of the first instruction region 41 is set to become smaller than the size of the cursor 40 as the distance between the first tomographic image Dk and the second tomographic image Dk+1 increases. For example, assuming that the cursor 40 has a spherical shape, the size of the first instruction region 41 is set to have the size of a circle generated by intersecting the cursor 40 assumed to have a spherical shape with the second tomographic image Dk+1. In this case, assuming that the distance between the first tomographic image Dk and the second tomographic image Dk+1 is D mm and the radius of the cursor 40 is R mm (R>D), the radius of the first instruction region 41 is $\sqrt{(R^2-D^2)}$ mm.

In a case where the first instruction region 41 is set, the second correction unit 26 sets the second instruction region on the second tomographic image Dk+1 based on the first instruction region 41 and the cursor 40, thereby correcting the boundary of the second region of interest extracted from the second tomographic image Dk+1 (Step ST6). Then, the process returns to Step ST4.

Figure 9:
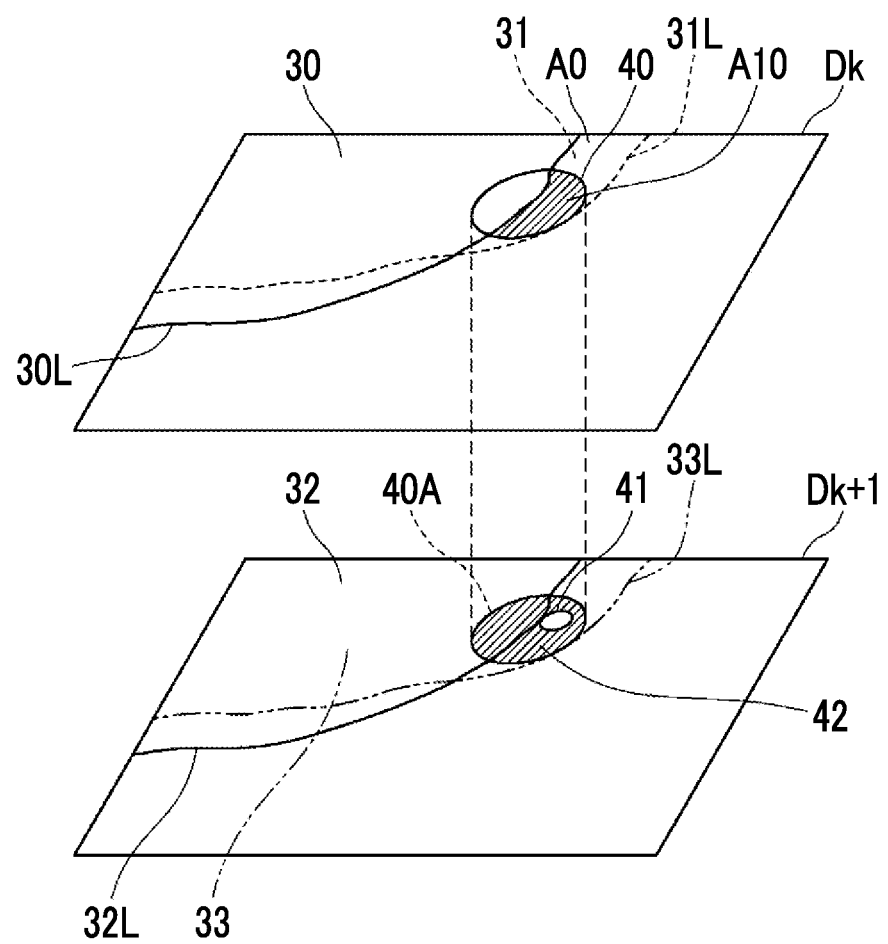
FIG. 9 is a diagram for explaining processing performed by a second correction unit in a case where the first correction region is an added region.

FIG. 9 is a diagram for explaining processing performed by the second correction unit 26 in a case where the first correction region is an added region. In addition, FIG. 9 shows the boundary 32L of a second region of interest 32 extracted from the second tomographic image Dk+1 and the boundary 33L of a actual region of interest 33. It is assumed that the second region of interest 32 is also a mask. The second correction unit 26 expands the first instruction region 41. In this case, the range to be expanded is within the range of the cursor-corresponding region 40A in the second tomographic image Dk+1. The dynamic contour method, the region expansion method, and the like are used for the expansion. As the dynamic contour method, a well-known algorithm such as the snake algorithm can be used. The snake algorithm is an algorithm in which the shape of a curve on an image plane is corrected by using an energy function expressed as the linear sum of internal energy and image energy on the curve such that the energy function is minimized, and thereby the contour line is extracted. Note that, the method thereof is not limited to the snake algorithm, and any dynamic contour method can be used.

In the present embodiment, as shown in FIG. 9, the first instruction region 41 in the second tomographic image Dk+1 is expanded. Thereby, the first instruction region 41 is expanded within the cursor-corresponding region 40A as shown in FIG. 9. The expansion is performed based on information regarding the inside of the cursor-corresponding region 40A in the second tomographic image Dk+1, specifically, the pixel value in the cursor-corresponding region 40A. Here, the change in pixel value becomes large in the boundary 33L of the actual region of interest 33 included in the second tomographic image Dk+1. Therefore, the first instruction region 41 is expanded to the boundary 33L of the actual region of interest 33 included in the second tomographic image Dk+1, within the cursor-corresponding region 40A. The expanded region is indicated by the diagonal lines. The region indicated by the diagonal lines is the second instruction region 42 which is added to the second region of interest 32 extracted from the second tomographic image Dk+1.

Figure 10:
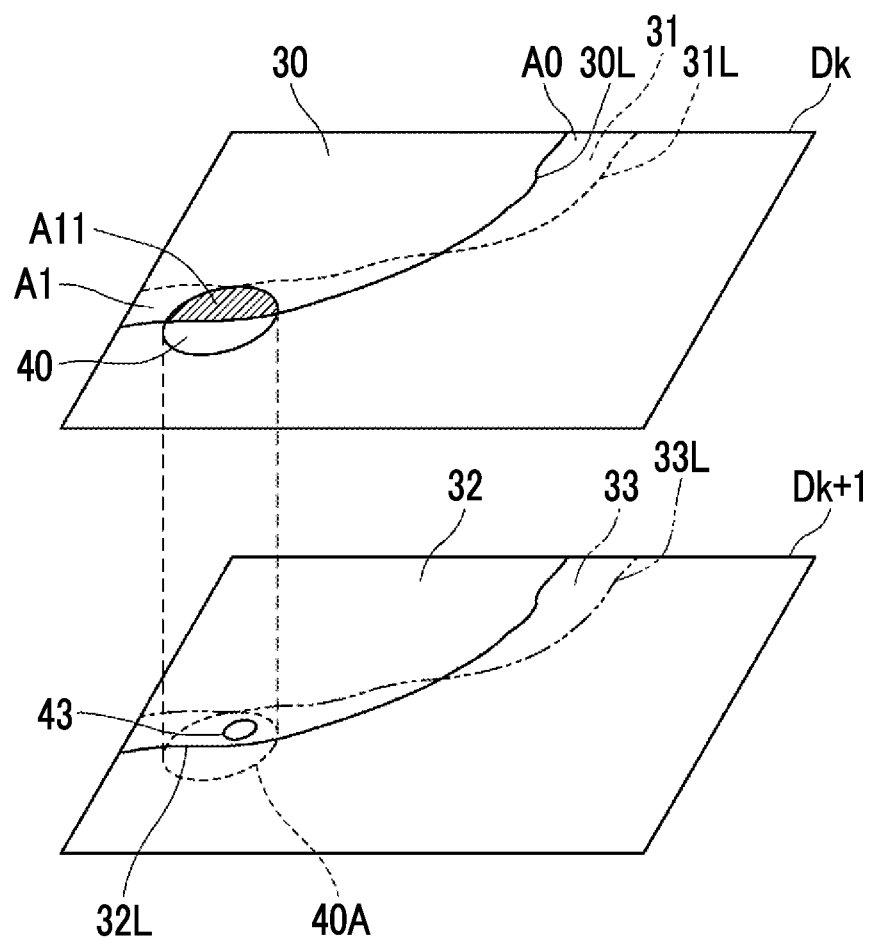
FIG. 10 is a diagram for explaining setting of the first instruction region in a case where the first correction region is a deleted region.

Next, processing in a case where the first correction region is a deleted region will be described. FIG. 10 is a diagram for explaining setting of the first instruction region in a case where the first correction region is a deleted region. As shown in FIG. 10, in a case where the first correction region A11 indicated by the diagonal lines in the cursor 40 is deleted, by using the cursor 40, from the region A1 by which the first region of interest 30 is over-extracted, the first instruction region setting unit 25 sets a circular first instruction region 43 having a size smaller than that of the cursor 40 at a position on the second tomographic image Dk+1 which corresponds to the deleted first correction region A11. As in the first instruction region 41, the size of the first instruction region 43 is set to become smaller than the size of the cursor 40 as the distance between the first tomographic image Dk and the second tomographic image Dk+1 increases.

In a case where the first instruction region 43 is set, the second correction unit 26 sets the second instruction region on the second tomographic image Dk+1 based on the first instruction region 43 and the cursor 40, thereby correcting the boundary of the second region of interest extracted from the second tomographic image Dk+1.

Figure 11:
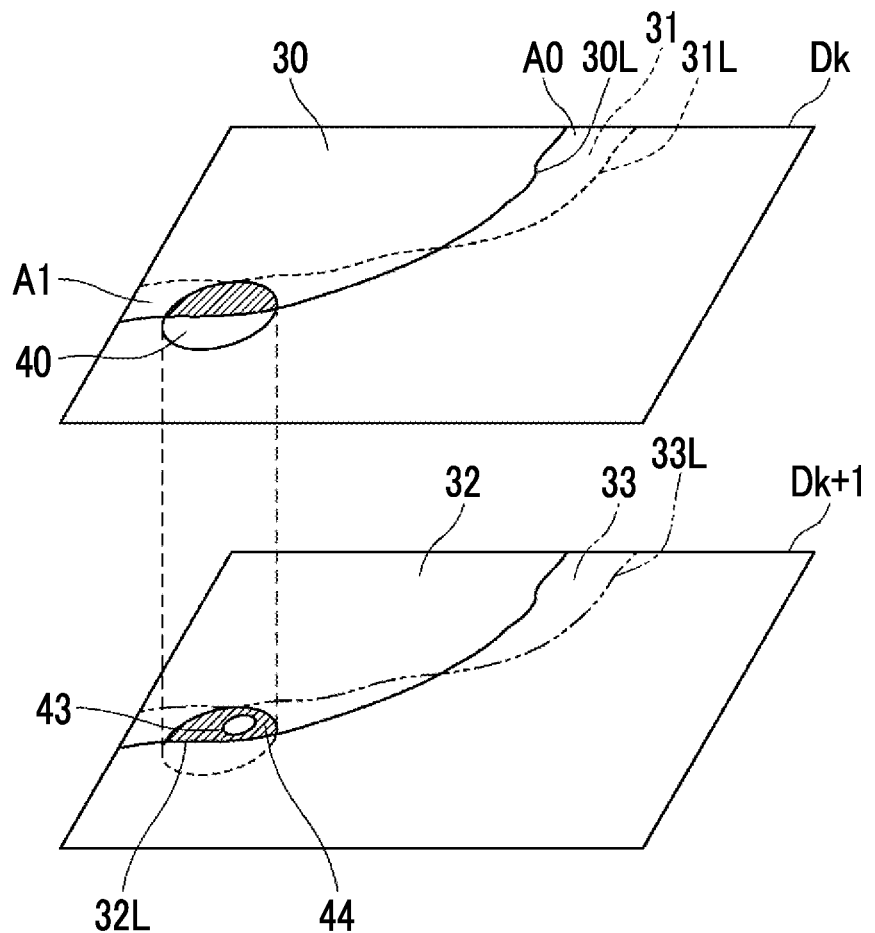
FIG. 11 is a diagram for explaining processing performed by the second correction unit in a case where the first correction region is a deleted region.

FIG. 11 is a diagram for explaining processing performed by the second correction unit 26 in a case where the first correction region is a deleted region. In addition, FIG. 11 shows the boundary 32L of the second region of interest 32 extracted from the second tomographic image Dk+1 and the boundary 33L of the actual region of interest 33. The second correction unit 26 expands the first instruction region 43, as in the first instruction region 41. Thereby, the first instruction region 43 is expanded within the cursor-corresponding region 40A as shown in FIG. 11. In this case, the change in pixel value becomes large in the boundary 33L of the actual region of interest 33 included in the second tomographic image Dk+1. Therefore, the first instruction region 43 is expanded to the boundary 33L of the actual region of interest 33 included in the second tomographic image Dk+1. The expanded region is indicated by the diagonal lines. The region indicated by the diagonal lines is the second instruction region 44 which is deleted with respect to the second region of interest 32 extracted from the second tomographic image Dk+1 and which corresponds to the first instruction region 43.

Figure 12:
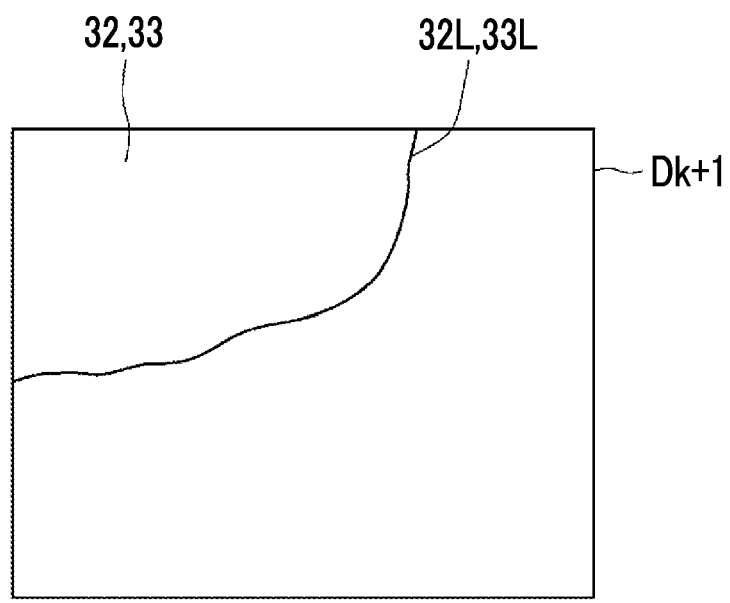
FIG. 12 is a diagram showing a state in which a boundary of the extracted second region of interest coincides with a boundary of an actual region of interest, in a second tomographic image.

In this way, the second correction unit 26 corrects the boundary 32L of the second region of interest 32 extracted from the second tomographic image Dk+1, as shown in FIG. 12, so that the boundary 32L of the extracted second region of interest 32 coincides with the boundary 33L of the actual region of interest 33 included in the second tomographic image Dk+1.

Figure 13:
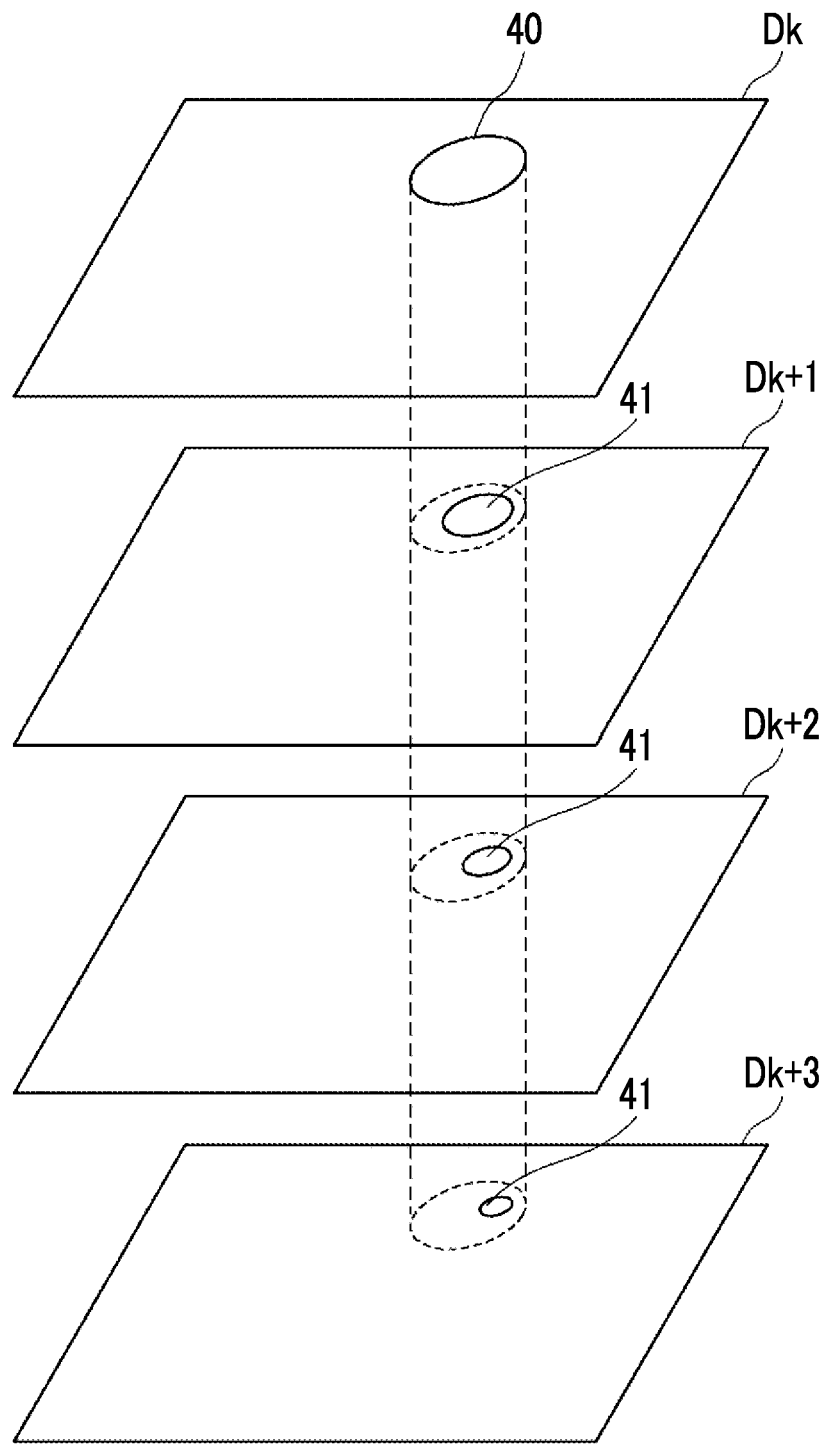
FIG. 13 is a diagram showing a state in which a size of the cursor decreases as the second tomographic image is positioned farther from the first tomographic image.

In the above, only the processing for one second tomographic image Dk+1 adjacent to the first tomographic image Dk has been described, but processing for a second tomographic image Dk−1 adjacent to the first tomographic image Dk side opposite to the second tomographic image Dk+1 may further be performed. Further, not only in one second tomographic image Dk+1 adjacent to the first tomographic image Dk, but also in a plurality of second tomographic images adjacent to both sides or one side of the first tomographic image Dk, the boundary of the region of interest may be corrected in the same manner as described above. The number of second tomographic images to be processed may be the number of images within a predetermined distance from the first tomographic image Dk. In this case, as shown in FIG. 13, as the second tomographic image is positioned farther from the first tomographic image Dk, the second tomographic image is more likely to have a different shape from the actual region of interest 31 included in the first tomographic image. Therefore, it is preferable to reduce the size of the first instruction region 41 corresponding to the cursor 40.

As described above, according to the present embodiment, the boundary 30L of the first region of interest 30 included in the displayed first tomographic image Dk is corrected by the correction instruction using the cursor 40 for the boundary 30L of the first region of interest 30. Further, the first instruction regions 41 and 43 are set on the at least one second tomographic image Dk+1 adjacent to the first tomographic image Dk, based on the first correction region A10 added or the first correction region A11 deleted by the correction in the first tomographic image Dk and the cursor 40. Furthermore, the second instruction regions 42 or the second instruction region 44 are set on the second tomographic image Dk+1 based on the first instruction regions 41 or the first instruction region 43 and the cursor 40, and thereby the boundary 32L of the second region of interest 32 extracted from the second tomographic image Dk+1 is corrected. Therefore, the operator can correct the boundary 32L of the second region of interest 32 in the second tomographic image Dk+1 in association with the boundary 30L of the first region of interest 30 only by correcting the boundary 30L of the first region of interest 30 extracted from the first tomographic image DK. As a result, according to the present embodiment, it is possible to correct the boundary of the region of interest by simple computation while reducing the burden on the operator.

In the above-described embodiment, the first instruction regions 41 and 43 are regions each obtained by reducing the cursor 40, but the first instruction regions 41 and 43 may be regions each consisting of one pixel.

Figure 14:
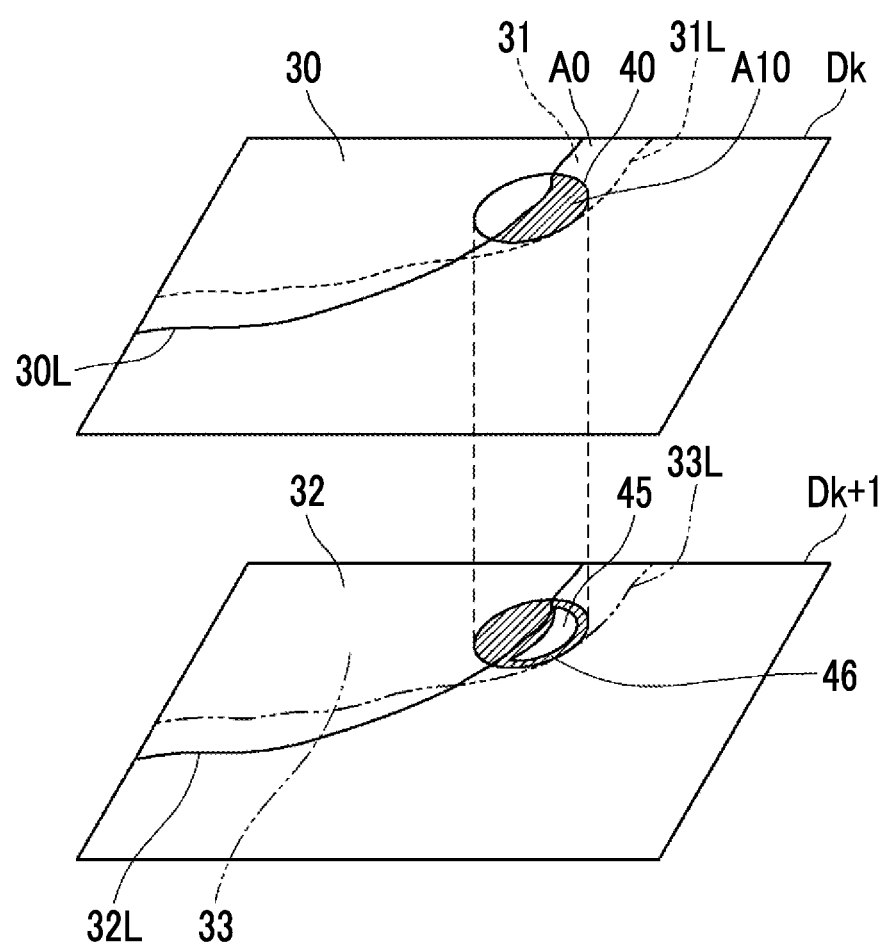
FIG. 14 is a diagram showing an example of another shape of the first instruction region.

Note that, in the above-described embodiment, the first instruction regions 41 and 43 have the same shape as the cursor 40, but the shape thereof is not limited thereto. For example, as shown in FIG. 14, in the first tomographic image Dk, the first instruction region 45 having a shape obtained by reducing the shape of the first correction region A10 in the cursor 40 may be set. In this case, the first instruction region 45 can be expanded and the second instruction region 46 can be added, in the same manner as the above-described embodiment.

In addition, in the above-described embodiment, the region correction apparatus comprises the region-of-interest extraction unit 22, but the present disclosure is not limited thereto. The region of interest may be extracted by a separate apparatus connected to the region correction apparatus via the network 4. Further, the three-dimensional image G0 to be acquired may include a region of interest already extracted.

Further, in the above-described embodiment, for example, as a hardware structure of a processing unit that executes various processing such as processing performed by the image acquisition unit 21, the region-of-interest extraction unit 22, the display controller 23, the first correction unit 24, the first instruction region setting unit 25, and the second correction unit 26, the following various processors may be used. Examples of the various processors include, as described above, a CPU which is a general-purpose processor functioning as various processing units by executing software (program), a programmable logic device (PLD) which is a processor having a changeable circuit configuration after manufacturing a field programmable gate array (FPGA) or the like, and a dedicated electric circuit such as an application specific integrated circuit (ASIC) which is a processor having a circuit configuration specifically designed to execute specific processing.

One processing unit may be configured by one of the various processors, or may be configured by a combination of two or more processors having the same type or different types (for example, a combination of a plurality of FPGAs or a combination of a CPU and an FPGA). Further, the plurality of processing units may be configured by one processor.

As an example in which the plurality of processing units are configured by one processor, firstly, as represented by a computer such as a client and server, there is a form in which one processor is configured by a combination of one or more CPUs and software, and the processor functions as the plurality of processing units. Secondly, as represented by a system on chip (SoC) or the like, there is a form in which a processor that realizes the function of the entire system including the plurality of processing units by one integrated circuit (IC) chip is used. As described above, the various processing units are configured by using one or more various processors as a hardware structure.

Further, as the hardware structure of the various processors, more specifically, an electric circuit (circuitry) in which circuit elements such as semiconductor elements are combined may be used.

What is claimed is:

1. A region correction apparatus comprising at least one processor,
wherein the processor is configured to:
display a first tomographic image of a three-dimensional image consisting of a plurality of tomographic images;
correct a boundary of a first region of interest extracted from the displayed first tomographic image, by a correction instruction using a correction instruction region for the boundary of the first region of interest;
set a first instruction region on at least one second tomographic image of the plurality of tomographic images based on a first correction region added or deleted by the correction in the first tomographic image and the correction instruction region, wherein the second tomographic image is included within a predetermined distance from the first tomographic image; and
correct a boundary of a second region of interest extracted from the second tomographic image by setting a second instruction region on the second tomographic image based on the first instruction region and the correction instruction region.

2. The region correction apparatus according to claim 1, wherein the processor is configured to set the first instruction region that has a size smaller than that of the correction instruction region as a distance between the first tomographic image and the second tomographic image increases.

3. The region correction apparatus according to claim 1, wherein the processor is configured to set the second instruction region by expanding the first instruction region based on information regarding an inside of a region of the second tomographic image corresponding to the correction instruction region.

4. The region correction apparatus according to claim 3, wherein the processor is configured to set the second instruction region having a shape corresponding to the boundary of the region of interest included in the second tomographic image.

5. The region correction apparatus according to claim 1, wherein the correction instruction region has a circular shape.

6. The region correction apparatus according to claim 1, wherein the processor is configured to extract a region of interest from each of the plurality of tomographic images.

7. A region correction method comprising:
displaying a first tomographic image of a three-dimensional image consisting of a plurality of tomographic images;
correcting a boundary of a first region of interest extracted from the displayed first tomographic image, by a correction instruction using a correction instruction region for the boundary of the first region of interest;
setting a first instruction region on at least one second tomographic image of the plurality of tomographic images based on a first correction region added or deleted by the correction in the first tomographic image and the correction instruction region, wherein the second tomographic image is included within a predetermined distance from the first tomographic image; and
correcting a boundary of a second region of interest extracted from the second tomographic image by setting a second instruction region on the second tomographic image based on the first instruction region and the correction instruction region.

8. A non-transitory computer-readable storage medium that stores a region correction program causing a computer to execute a process, the process comprising:
displaying a first tomographic image of a three-dimensional image consisting of a plurality of tomographic images;
correcting a boundary of a first region of interest extracted from the displayed first tomographic image, by a correction instruction using a correction instruction region for the boundary of the first region of interest;
setting a first instruction region on at least one second tomographic image of the plurality of tomographic images based on a first correction region added or deleted by the correction in the first tomographic image and the correction instruction region, wherein the second tomographic image is included within a predetermined distance from the first tomographic image; and
correcting a boundary of a second region of interest extracted from the second tomographic image by setting a second instruction region on the second tomographic image based on the first instruction region and the correction instruction region.

* * * * *